United States Patent
Davidson et al.

(10) Patent No.: US 6,238,491 B1
(45) Date of Patent: May 29, 2001

(54) NIOBIUM-TITANIUM-ZIRCONIUM-MOLYBDENUM (NBTIZRMO) ALLOYS FOR DENTAL AND OTHER MEDICAL DEVICE APPLICATIONS

(75) Inventors: James A. Davidson, Germantown, TN (US); Lee H. Tuneberg, Sheboygan, WI (US)

(73) Assignee: DaviTech, Inc., Germantown, TN (US)

( * ) Notice: Subject to any disclaimer, the term of this patent is extended or adjusted under 35 U.S.C. 154(b) by 0 days.

(21) Appl. No.: 09/305,881

(22) Filed: May 5, 1999

(51) Int. Cl.$^7$ .............................. C22C 27/02; A61C 3/00; A61B 17/56
(52) U.S. Cl. .................... 148/237; 148/422; 420/426; 428/698; 433/3; 433/8; 606/76
(58) Field of Search .................... 148/422, 237, 148/421; 420/580, 425, 426, 421; 428/698; 433/201.1, 173, 2, 8–23; 606/76, 77; 623/2

(56) References Cited

U.S. PATENT DOCUMENTS

| | | | |
|---|---|---|---|
| Re. 35,863 | 7/1998 | Sachdeva et al. | 433/8 |
| 2,822,268 | * 2/1958 | Hix | 75/174 |
| 3,230,119 | * 1/1966 | Gemmell et al. | 148/158 |
| 3,346,379 | * 10/1967 | Rhodin, Jr. | 75/174 |
| 3,644,153 | * 2/1972 | Rausch et al. | 148/31.5 |
| 4,040,129 | * 8/1977 | Steinmann et al. | 3/1.9 |
| 4,511,411 | 4/1985 | Brunner et al. | 148/20.3 |
| 4,592,725 | 6/1986 | Goshgarian | 433/7 |
| 4,665,906 | 5/1987 | Jervis | 128/92 |
| 4,708,646 | 11/1987 | Jasper | 443/19 |
| 4,857,269 | 8/1989 | Wang et al. | 420/417 |
| 4,952,236 | * 8/1990 | Wang et al. | 148/2 |
| 5,037,438 | 8/1991 | Davidson | 623/18 |
| 5,064,370 | 11/1991 | Jones | 433/21 |
| 5,067,897 | 11/1991 | Tuneberg | 433/8 |
| 5,067,957 | 11/1991 | Jervis | 606/108 |
| 5,167,499 | 12/1992 | Arndt et al. | 433/7 |
| 5,169,597 | * 12/1992 | Davidson et al. | 428/613 |
| 5,179,174 | * 1/1993 | Elton | 525/409 |
| 5,232,361 | 8/1993 | Sachdeva et al. | 433/8 |
| 5,282,852 | 2/1994 | Capetan et al. | 623/6 |
| 5,312,247 | 5/1994 | Sachdeva et al. | 433/7 |
| 5,334,264 | 8/1994 | Meletis | 148/222 |
| 5,370,694 | 12/1994 | Davidson | 623/16 |
| 5,372,660 | 12/1994 | Davidson et al. | 148/421 |
| 5,380,200 | 1/1995 | Heath et al. | 443/102 |
| 5,415,704 | 5/1995 | Davidson | 148/316 |
| 5,419,984 | 5/1995 | Chaloner-Gill et al. | 429/192 |
| 5,441,409 | 8/1995 | Tuneberg | 433/23 |
| 5,464,362 | 11/1995 | Heath et al. | 451/48 |
| 5,496,359 | 3/1996 | Davidson | 607/115 |

(List continued on next page.)

FOREIGN PATENT DOCUMENTS 9638097   12/1996  (WO).

OTHER PUBLICATIONS

Brochure: Tiadyne™ 3510; Teledyne Wah Chang; Jan. 10 1994.

(List continued on next page.)

Primary Examiner—George Wyszomierski
Assistant Examiner—Janelle Combs-Morillo
(74) Attorney, Agent, or Firm—Fulbright & Jaworski LLP (57) ABSTRACT

The present invention is a medical implant or device fabricated, in any manner, from a niobium (Nb)—titanium (Ti)—zirconium (Zr)—Molybdenum (Mo) alloy (NbTiZrMo alloy). The implant or device has components at least partially fabricated from a metal alloy comprising a) between about 29 and 70 weight percent Nb; b) between about 10 and 46 weight percent Zr; c) between about 3 and 15 weight percent Mo; and a balance of titanium. The inventive alloy provides for a uniform beta structure which is corrosion resistant, and can be readily processed to develop high-strength and low-modulus, with the ability for conversion oxidation or nitridization surface hardening of the medical implant or device.

17 Claims, 5 Drawing Sheets

U.S. PATENT DOCUMENTS

| | | | |
|---|---|---|---|
| 5,527,205 | 6/1996 | Heath et al. | 451/48 |
| 5,545,227 | 8/1996 | Davidson et al. | 623/16 |
| 5,562,730 * | 10/1996 | Davidson | 623/3 |
| 5,628,674 | 5/1997 | Heath et al. | 451/48 |
| 5,655,950 | 8/1997 | Heath et al. | 451/48 |
| 5,904,480 * | 5/1999 | Farzin-Nia et al. | 433/20 |
| B1 4,659,309 | 5/1993 | Merkel et al. | 443/9 |

OTHER PUBLICATIONS

Ito A., et al. Mechanical Properties and Cytocompatability of New Titanium Alloys in The System Ti–Zr–Nb–Ta–Pd and Ti–Sn–Nb–Ta–Pd; $10^{th}$ European Conference on Biomaterials, Davos, Switzerland, Sep. 8 –Nov. 1993.

Titanium '92 Science and Technology, vol. 1; Eds. F.H. Froes & I.L. Caplan; Proceedings Seventh World Titanium Conference, San Diego, CA, Jun.29 –Jul. 2, 1992.

Abstract from Journal of the Japan Institute of Metals: Effect of Alloying Elements on Mechanical Properties of Titanium Alloys for Medical Implants 57,(3) Mar. 1993, pp. 332–337; and Abstracts from Journal of Mechanical Engineering Laboratory (Japan): Development of New Titanium Alloys for Medical Implants. I. Microstructure and Mechanical Properties; 45(5), Sep. 1992, pp. 397–416; II. Anodic Polarization Properties in Acid Environment, pp. 417–430; and III. Corrosion Resistance in Physiological Saline Solution, pp. 431–443.

A. Yamamoto, et al. Cytotoxicity evaluation of 43 metals salts using murine fibroblasts and osteoblastic cells; John Wiley & Sons, Inc. (1998).

Chapter 1 Corrosion of Surgical Implants in vivo and in vitro Tests; S. G. Steinmann; Evaluation of Biomaterials, Eds. G. D. Winter et al.; John Wiley & Sons Ltd (1980).

Patrick G. Laing et al. Tissue Reaction in Rabbit Muscle Exposed to Metallic Impants; J. Biomed. Mater. Res.; vol. 1, pp 135–149 (1967).

T. P. Hoar and D.C. Mears; Corrosion–resistant alloys in chloride solutions; materials for surgical implants; pp 486–510.

Catalog: Materials Engineering; Materials Selector 1989 (Dec. 1988).

M. Pourbaix; Figs. 4 and 5; Biomaterials (1984).

E.W. Collings; The Physical Metallurgy of Titanium Alloys; American Society for Metals; selected pages.

* cited by examiner

NIOBIUM-TITANIUM-ZIRCONIUM-MOLYBDENUM (NBTIZRMO) ALLOYS FOR DENTAL AND OTHER MEDICAL DEVICE APPLICATIONS

FIELD OF THE INVENTION

The present invention relates to niobium alloys suitable for use in the construction of dental and other medical implants, and devices. More specifically, this invention relates to a bio-compatible, corrosion-resistant niobium-based NbTiZrMo alloy for use in medical device applications which can be cold-worked to a high level of strength and flexibility for improving performance of orthodontic, endodontic, dental, orthopaedic, cardiovascular, and other medical implants and devices.

BACKGROUND OF THE INVENTION

Niobium is a corrosion-resistant material which can be expected to be biocompatible in the living body (A. Yamamoto, et. al., J. Biomed. Mater. Res., 1998). Niobium (Nb), in fact has been added as an alloy constituent inntitanium alloys currently used in medical implant and device applications, such as Ti13Nb13Zr and Ti7Nb6Al (protasul 100™). But niobium in the unalloyed condition is a relatively low-strength metal with a tensile strength ranging as high as 94 ksi and as low as 13 ksi (*Materials Engineering*, Materials Selector, 1989, Pentum Pub., Inc. Cleveland, Ohio, December 1988). Typically the strength of niobium lies between 48 and 85 ksi, thus, although a biocompatible metal, niobium has not been recognized as an implant metal.

A niobium alloy is an alloy with niobium and at least one other element, and where the niobium represents an equal or majority amount, by weight in the alloy. Niobium, when alloyed with titanium or zirconium can produce, in the proper concentration, a superconducting metal, and is thus used primarily in non-medical applications. The presence of zirconium (Zr) in niobium results in higher mechanical properties. The addition of titanium (Ti) to niobium reduces the melting temperature making it easier to process. The presence of titanium in niobium can also improve corrosion resistance, particularly in lower pH environments (Prourbaix, 1984). Niobium with moderate levels of titanium tends to maintain a more ductile, readily cold-workable, and easy to process alloy. This combination tends to stabilize a desired beta phase at room temperature. Titanium and zirconium also reduce the melting temperature of the Nb alloy, and improves the ability of molybdenum to mix during melting. Because Nb and Zr are closer in density to Mo, the Mo will have a reduced tendency to segregate during melting compared to Mo in titanium alloys. Further the addition of zirconium in sufficient quantity helps to further stabilize the desired beta phase, as well as improving strength. The zirconium also produces a more stable passive surface oxide to improve corrosion resistance and also allows for conversion oxidation or nitridization of the surface. Such conversion processes can produce a hard, abrasion-resistant, inert, oxide or nitride ceramic surface layer. The amount of Nb preferred in the present invention is between about 29 to 70 weight percent, and with Zr between about 10 and 46 weight percent. Finally, the presence of molybdenum in titanium can improve corrosion resistance in chloride-containing environments, when present at levels above about 3 weight percent and less than about 15 weight percent. Because the invention niobium alloy contains titanium, an amount of Mo is also included in the invention NbTiZrMo alloy system. Further, Mo is a strong stabilizer of the beta phase and its presence further assures the strong tendency for a stable, desirable beta phase to form at 500° C. or below.

Considering the metallurgical factors, the present invention describes a niobium alloy containing titanium, zirconium, and molybdenum for use in medical implants and devices. The composition specifically avoids the use of known allergens, toxins, or carcinogens, such as Ni, Cr, Co and V, and avoids aluminum which has been associated with an adverse interference of neurological processes. Other less bio-compatible elements such as tin, iron, and copper are also excluded from the composition of the present invention Nb alloy to optimize corrosion resistance and bio-compatibility.

The usefulness of the invention NbTiZrMo alloy is to develop a stable corrosion-resistant, beta structure which is tough, and which can be strengthened from cold-working, and will additionally result in a reduction of elastic modulus from the cold-working process. Further, the presence of a uniform beta phase (versus alpha plus beta) at about 500° C. improves the uniformity and effectiveness of conversion oxide surface layers found at that temperature. Thus the resultant NbTiZrMo alloy can be processed to be tough and fracture resistant or high-strength and flexible (low modulus) for medical device applications requiring strong, resilient materials such as orthodontic arch wire and other orthodontic devices, endodontic dental files for root canals, trauma and spinal plating and screws, dental implants and posts, pacing leads, vascular stents, and other medical devices. Higher strength and greater flexibility improve the resistance of such devices to breakage, and can improve load transfer to adjacent tissue.

Specifically, the invention niobium alloy is a NbTiZrMo alloy with no other alloy constituent exceeding the amount weight percent of niobium, and comprising a combination between about 10 and 46 percent of Zr, and about 3 to 15 weight percent Mo, and the balance titanium. Contaminants, each, less than about 1 percent, can be present, not exceeding a total of about 3 weight percent, and include Si, P, Cu, Fe, Ta, Hv Sn, or Pd.

The author is not aware of any specific niobium-molybdenum alloys, particularly NbTiZrMo alloys currently used in or described for medical device applications. However there are a variety of titanium and zirconium alloys currently in use or that have been proposed, and which may include Nb or Mo in the composition. These alloys are described in the following sections:

Examples of titanium alloy used for medical devices, include a low-modulus, room temperature beta titanium alloy for orthodontic arch wire as described in U.S. Pat. No. 4,197,643. This patent describes the use of Mo, Nb, Ta additionally, the use of Mn, Fe, Cr, Co, Ni, Cu, Al and Zr. However this is a titanium-based alloy material and not a niobium alloy. Alloy strength is achieved by aging to precipitate the alpha phase or cold working. The preferred composition is Ti-11.5Mo-6Zi-4.5Sn, commonly called Beta III a (or TMA) and which does not even contain niobium. U.S. Pat. No. 5,312,247 describes a shape-memory or super elastic alloy having a predetermined activation temperature for use in orthopedic applications. This patent further describes the use of nickel-titanium based and titanium-molybdenum based alloys but as in the previous example, is not a niobium alloy. The use of nickel-containing metals is undesirable, not only in orthodontics, but in most medical device applicant, and even jewelry, due to the common occurrence of nickel sensitivity of patients. The applicants are unaware of any niobium-based alloys with shape memory properties, at least at temperatures useful in the human body. Nitinol is a commonly used Ti—Ni alloy with shape memory behavior that is used in many types of medical device applications. However, this highly elastic alloy is less than optimum with respect to other alternative available titanium alloys or the invention niobium alloy because the high concentrations of nickel interfere with the corrosion resistance properties of the alloys and the presence of the nickel can induce a sensitivity problem. Additionally nickel can interfere with magnetic resonance imaging quality. U.S. Pat. No. 5,232,361 and reissue Re35,863 are directed to an orthodontic bracket formulated of at least one of a group of alloys based on Ti, Zr, Si, B, Be, Cr, Nb and Co in a composition in which at least one of these elements exists in a range of between 40 weight percent and greater than 99 weight percent. Mo is not included in the preferred composition as it is in the present invention, and a Ti-based orthodontic bracket containing at least 45 weight percent titanium is given as an example. Other examples include alloys with at least 80 weight percent Ti with the addition of Al, V, Fe and/or Nb, and even a 99 weight percent Ti alloy. Once again the use of molybdenum or specific use of Nb-base alloys is not described. Further, allowable alloy constituents, in the '361 patent allow for bio-compatibility which is less than optimal, and which differs from the present NbTiZrMo patent.

Other examples of shape memory alloys include those described in U.S. Pat. Nos. 4,665,906 and 5,067,957 which describe medical devices and methods of installation using a non-specific shape memory alloy which displays stress induced martensitic behavior, versus an activation temperature. The present invention Nb alloy does not exhibit shape memory behavior, and contains Mo to improve corrosion resistance.

PCTAUS 96/00016 (Pub. No., 96/38097) by Farzin-Nia and Sachdeva describes a dental or orthodontic article comprising an alloy having a primary constituent of at least one of the group consisting of Ti, Zr, Si, Mo, Co, Nb, and Be; and at least one secondary element selected from the group consisting of Ta, Cu, Al, V, Pd, Hf and Fe, and where the primary constituent is in the range of about 30 to 85 percent by weight. Subsequent claims specify the preference for a Ti or Zr base alloy. The present invention NbTiZrMo alloy does not contain the required second constituent described by the Farzin-Nia/Sachdeva PCT. Additionally, the present patent teaches against the use of Be, Cu, Co, Al and V as constituents in the composition due to adverse bio-compatibility reasons. Further, the present alloy describes the total amount of Nb, Ti, Zr and Mo to be 100 percent, and well above the 85 percent maximum described by the Farzin-Nia/Sachdeva PCT. Other patents refer to metal alloy compositions for endodontic dental files. U.S. Pat. No. 5,380,200 relates to a bi-metallic dental file with a flexible core comprising NiTi alloy, stainless steel, or any Ti alloy. The present invention does not describe a bimetallic file nor is it a nickel-titanium or titanium alloy material. The present invention describes a single niobium-based NbTiZrMo alloy, but which could be additionally useful as a core material as described by the '200 patent.

U.S. Pat. No. 5,655,950; 5,628,674; 5,527,205; and 5,464,362 describe the machining and grinding method for a dental file made of a metallic material comprised of at least 40 percent titanium and which has a diameter less than about 0.07 inches. In contrast, the present invention describes aNb-based alloy and is comprised of less than about 40 percent titanium. Further, the above referenced grinding and machining methods, or any type of grinding, machining, stamping, forging or other manufacturing method can be utilized with the invention NbTiZrMo alloy.

Other titanium alloy device materials include those for orthopedic devices. For example, Ti-6Al-7Nb was developed several years ago to eliminate the potentially toxic effects of vanadium which is present in commonly used Ti-6Al-4V alloy (M. Semlitsch, Biomet. Technik, 1985). However, aluminum, which has been associated with Alzheimer and other neurological-related diseases, remains in this alloy. In view of this problem, others have proposed titanium alloy compositions with lower or no aluminum, or the absence of other toxic or carcinogenic elements associated with adverse responses to body function. As in the present invention alloy, this aspect of bio-compatibility has also been combined with an additional focus to reduce the elastic modulus of a niobium alloy (versus titanium alloys described in the prior art).

An early example of an improved titanium alloy for implants was discussed in the U.S. Pat. No. 4,040,129 in which bone and dental implants having full tissue compatibility were described as being composed of a first component of about 3 to 30 weight percent selected from the group Nb, Ta, Cr, Mo and/or Al, and a second component of Ti and/or Zr; wherein the sum of the Cr, Mo and Al is less than 20 weight percent and weights of Ti and/or Zr is less than 75 weight percent. This alloy was also free of Cu, Co, Ni, V and Sn. Examples described in the patent include Ti-9Nb-11Cr-3Al and Ti4 Mo-48Zr. However, the present invention is a Nb-based alloy and which contains an amount of Nb and Mo greater than the 30 weight percent taught by the '129 patent. Additionally, in U.S. Pat. No. 4,040,129, the benefit and desirability of a lower elastic modulus of the described alloy was not discussed. Improved bio-compatibility was described. However, aluminum is allowed in the composition which, as mentioned above, has since been found to be associated with adverse neurological responses.

A more recent patent, U.S. Pat. No. 4,857,269, also deals with the desirability of low elastic modules in medical devices. This patent describes a titanium based alloy (versus Nb-base) consisting of an amount of up to 24 weight percent of isomorphous beta stabilizers Mo, Ta, Nb and Zr, providing that the molybdenum, if present, is at least 10 weight percent, and when present with zirconium, is between 10 and 13 weight percent with the zirconium being between 5 and 7 weight percent. Additionally, the same titanium based alloy also has up to 3 weight percent eutectoid beta stabilizers selected from Fe, Mn, Cr, Co and Ni, wherein the combined amount of isomorphous and eutectoid beta stabilizers is at least 1.2 weight percent. Optionally, up to 3 weight percent aluminum and lanthanum can be present in the alloy with the elastic modules not exceeding 100 Gpa (14.5 Msi). Examples include Ti-10-20Nb-1-4Z-2Fe-0.5Al (TMZF™). These elemental compositions fall well outside the ranges of the present invention Nb alloy.

Various investigators in recent years have come to better understand the inherent bio-compatibility of various elements. Laing, et. al., in 1967, noted minor tissue reaction to implanted Ti, Zr, Nb, Ta and Ti alloys and a slightly greater reaction to pure, unalloyed Mo, V, Co, Ni, Mo and Fe. In another study in 1980, Steinemann concluded that vital elements Ti, Nb, Zr, Ta and Ti alloys, and Pt showed optimum bio-compatibility and that the slightly less bio-compatible elements included Al, Fe, Mo, Ag, Au and Co alloys and stainless steel. It was further noted that Co, Ni, Cu and V could be considered toxic. Hoars and Mears (1966) and Pourbaix (1984), based on electrochemical stability, suggested the use of Ti, Nb, Zr, and Ta as elemental constituents for improved bio-compatibility. However, it is important to note that Ti—Mo alloys were included as acceptable materials and this was supported by comparative corrosion data between Ti and Ti-16Mo-3Nb-3Al in which the Ti—Mo alloy showed improved corrosion resistance. Thus as mentioned earlier, the presence of Mo in titanium alloys can actually be beneficial from the standpoint of corrosion and bio-compatibility. The ternary alloy system of Ti, Zr, and Nb is described (Doi, et. al. In *Titanium Alloys*, by F. W. Collings, ASM, 1986) with respect to the various phases which form at various temperatures. However, the quatinary system, NbTiZrMo is not discussed. The presence of the Mo will further stabilize the desired beta phase of the invention alloy, particularly at the typical temperature used (about 500° C. to 600° C.) for conversion oxidation which can form an inert, hard surface oxide surface layer. A uniform beta phase versus an alpha plus beta phase will allow for more uniform development of this conversion oxide surface layer, and thus improved oxide (or nitride) integrity.

In an effort to improve both the bio-compatibility and to reduce elastic modulus in a titanium alloy, Davidson and Kovacs (U.S. Pat. No. 5,169,597) developed a medical implant titanium alloy with 10–20 weight percent Nb, or 30–50 weight percent Nb and 13–20 weight percent Zr, or sufficient Nb and/or Zr to act as a beta stabilizer by slowing transformation of beta (U.S. Pat. No. 5,545,227), where toxic elements are excluded from the alloy. However, there is no mention of the inclusion of Mo in the comparison as for the present invention Nb alloy. The preferred example is Ti-13Nb-13Zr (Ti 1313™). Tantanum can also be used in the '227 patent as a replacement for niobium where the sum of Nb and Ta is 10–20 weight percent of the alloy. But a niobium based alloy is not described. Subsequent continuation-in-part patents, describing this type of alloy for cardiovascular and dental implant devices, also exist and are considered herein with respect to prior art. All of these patents describe the use of Ti, Nb, and/or Zr. However, the use of a niobium-based NbTiZrMo described in the present invention alloy are not taught in these prior art patents. Others such as I. A. Okazaki, T. Tateishi and Y. Ito, have also proposed Ti-based alloy compositions including Ti-15Zr-4Nb-2Ta-0.2Pd and variations of the type Ti-5Zr-8Nb-2Ta-10–15-Zr-4–8-Nb-2–4 Ta, Ti-10–20Sn-4–8Nb-Ta-0.2Pd, and Ti-10–20 Zr4–8Nb-0.2Pd. Once again, none of these compositions are within the Nb alloy composition range described in the present patent.

Teledyne Wah Change Albany, a major supplier of titanium zirconium, and niobium, and their alloys, developed a Ti-35Nb-10Zr alloy. Again this is a titanium based alloy outside the composition ranges of the present patent, and does not include Mo.

Many investigators have studied and reported methods to harden titanium alloys, primarily through surface hardening processes. In addition to the improved properties of the invention alloy, the invention Nb alloy is also designed to be surface hardened. Prior art surface hardening methods include a wide range of overlay coating methods such as chemical and physical vapor depositions methods. These methods, however, require too high or too low a temperature, that results in metallurgical changes and less than optimum attachment of the hard, deposited, surface coating, or require the use of an interlayer to improve attachment of the hard surface coating. Alternatively, oxidation and nitriding methods can form a natural, more uniform, conversion surface oxide or nitride with a hard, built-in oxygen or oxygen rich, hardened metal interlayer just below the hard surface layer. Examples of these are described in U.S. Pat. No. 5,372,660 for zirconium-containing titanium alloys, U.S. Pat. No. 5,037,438 for oxygen surface hardening of Zr and Zr-Nb alloys for implant bearing surfaces, and U.S. Pat. No. 5,152,794 for oxidation and nitriding of zirconium or zirconium alloy trauma devices with a surface layer 1–5 microns thick. Other similar patents exist for zirconium-containing titanium alloys and Zr based Zr-Nb alloys used in orthopedic and cardiovascular devices. See, for example, U.S. Pat. Nos. 5,282,852; 5,370,694 and 5,496,359. None of these conversion oxidation and nitridization patents teach the use of this surface hardening method for Nb-base alloys as in the present invention, nor the use of Nb alloys containing Mo.

Internal oxidation is also described in U.S. Pat. No. 5,415,704, whereas U.S. Pat. No. 5,498,302 describes internal nitrization methods to harden a surface, but without the presence of a hard outer oxide or nitride layer. Unlike oxygen or nitrogen diffusion methods which produce interstitial strengthening of the metal, internal oxidization or nitridization, using solute levels of more oxidizable or nitridable elements in quantities less than 2 weight percent, actually form submicron oxide or nitride dispersions to produce the hardening. Other nitridizing processes to harden the surface are described in U.S. Pat. No. 5,419,984 for stainless steel, in U.S. Pat. No. 4,511,411 for titanium alloys using and autoclave containing nitrogen, and U.S. Pat. No. 5,334,264 which uses enhanced plasma nitriding methods. There are also studies of oxygen diffusion hardening of Ti, Ti-6Al-4V and Ti6Nb-7V alloys (Streicher), and the use of N-ion implantation (Sioshanchi) which produces a much less effectively hardened and non-uniform surface. A wide variety of surface nitriding and oxidation options are available and know to those skilled in the art. In the non-medical literature, studies by Wallwork and Jenkins, 1959, exist on the oxidation of zirconium and titanium alloys to produce a hard, well attached conversion surface oxide diffusion bonded to the metal substrate. However, these oxidation characteristics were obtained in an effort to reduce (resist) this process, and not to intentionally form the surface oxide to form a hard, protective, wear-resistant surface layer. Importantly, Nb-based alloys of the present invention were not described. Bania and Parris (Timet, Inc., Beta 21S, Vol. II, 1990 Ti Conf.) investigated various Ti—Mo, Ti—Cr, Ti—Hf, Ti—Nb alloys and other Ti-based alloys with respect to oxidation resistance that leads to the optimum composition of the beta21S alloy (Ti-5Mo-2.8Nb-3Al). Specific combinations of Ti, Mo, and Nb were not investigated for implant applications or applications with optimal combinations of strength, hardness, and elastic modulus. Importantly, a niobium based NbTiZrMo alloy of the present invention was not described. The use of alloy, Ti-21S, has been proposed for medical implants (B3itambri and Shetty, 1994 Soc. Biomat. Pg. 195). However, the presence of Al in Ti-21S, along with only a marginal reduction in elastic modulus in the age-hardened condition, verses the elastic modulus of Ti-6Al-4V, renders this alloy less than optimum for medical implant applications. Thus, the above discussion illustrates the non-obviousness of the inventive NbTiZrMo compositions as being useful for medical implant and device applications.

SUMMARY OF THE INVENTION

The present invention is a novel niobium based NbTiZrMo alloy suitable for use in the fabrication of medical implants and devices. The invention alloy is a corrosion-resistant bio-compatible, tough, high-strength, low-modulus, niobium-based alloy composed of Nb,Ti,Zr, and Mo and, where the amount of Nb is between about 29 and 70 weight percent, where Zr is between about 10 and 46 weight percent, where Mo is between about 3 and 15 weight percent, and where the balance is Ti. In addition, oxygen, nitrogen or carbon can be increased for interstitial strengthening. Medical implants and devices manufactured from these niobium-based alloys can be readily cold-worked to increase strength, and have improved meltability, processability, toughness, flexibility, corrosion resistance, and the ability to be conversion surface hardened via oxidation or nitridization.

BRIEF DESCRIPTION OF THE DRAWINGS

The invention will become more apparent when the detailed description of exemplary embodiments is considered in conjunction with the appended drawings, in which.

DETAILED DESCRIPTION OF THE PREFERRED EMBODIMENTS

The inventive alloy can be produced by combining, as commercially pure components, niobium, titanium, zirconium and molybdenum in the appropriate proportions under vacuum or inert melting or reducing conditions. The method for alloy production, such as casting, powder metallurgy, etc. are well known to those of ordinary skill in the art of metallurgy and the production of the alloy requires no special skills or precautions beyond the materials, proportions and techniques described below.

The present invention comprises a bio-compatible, tough, beta, high-strength, low-modulus, uniform niobium base NbTiZrMo alloy for the manufacture of medical implants and devices having improved corrosion resistance due to the combined addition of 3–15 weight percent molybdenum (Mo) and the relatively large amounts of titanium and zirconium, in which the latter (Zr) additionally allows for the surface hardening of a medical implant or device manufactured from the inventive alloy. If desired, the amount of molybdenum can be adjusted such that the elastic modulus of the alloy is minimized.

FIG. 7 (Ref. Doi, et. al., and Collins) shows the ternary phase diagram for the TiZrNb alloy system (atomic percent). Between about 900° C. and 500° C. this system exhibits a spinodal decomposition along the Nb-Zr binary between about 25 to 47 at percent Zr. The addition of titanium eliminates the tendency for the spinodal which may compromise high-temperature processing. The levels of Zr and Ti in the invention NbTiZrMo Nb alloy have been chosen to avoid this spinodal phase separation. The addition of a comparable amount of titanium to niobium also reduces the tendency for strain-induced martensitic transformation in this binary system. The addition of a large amount of Zr (above about 10 weight percent) also helps to suppress this effect and also helps promote the stabilization of a desired uniform beta phase, to improve the cold-workability of the invention NbTiZrMo alloy. Notice in FIG. 7 that an equilibrium alpha plus beta phase is present for most Nb-Ti-Zr compositions below about 500° C. Thus the present invention NbTiZrMo alloy has the addition of Mo, a very strong beta stabilizer, to assure that a uniform beta phase is relatively stable below 500° C. Further, as mentioned previously the presence of Mo in the Ti constituent of the invention alloy can be expected to improve corrosion resistance in chloride-containing aqueous environments, typical of the body environment, and within crevices, typical of assembled dental and orthodontic devices. Thus the invention NbTiZrMo alloy incorporates Mo between about 3 and 5 weight percent. This is also within a range that can help reduce the elastic modulus for the relative percent of Mo within the Ti constituent in the invention alloy.

Another advantage of a NbTiZrMo alloy system relates to the melting temperatures and density of the alloy constituents and the favorable influence on melting the alloy with improved mixing, uniformity and with less gravimetric segregation. Lighter weight titanium alloys tend to exhibit poor or difficult ming behavior with heavier alloy constituents such as Mo, Zr and Nb. Examples include the beta III (TMA), Ti-15Mo,Ti13Nb 13Zr, and TMZF (™Howmedica). These alloys have a level of Mo of about 11 to 15 weight percent or Zr, and Nb of 5 to 13 weight percent. Table 1 below summarizes the melting temperature and density of these elemental constituents.

TABLE 1

Melting temperature and density of Nb, Ti, Zr, and Mo.

| Element | Melting Temperature (0 C.) | Density (grams/cm³) |
|---|---|---|
| Niobium (Nb) | 2469 | 8.57 |
| Zirconium (Zr) | 1855 | 6.5 |
| Molybdenum (Mo) | 2625 | 10.2 |
| Titanium (Ti) | 1670 | 4.54 |

If Mo is added to titanium, the mismatch in melting temperature makes it very difficult to melt, and multiple melting operations are required to assure good mixing into the Ti base material. An additional complication in this case is the large mismatch in density where the heavier Mo tends to gravimetrically settle toward the bottom of the ingot. In the invention Nb-based NbTiZrMo alloy, the higher melting temperature of the Nb, and to some degree, Zr, improves the ability of the Mo to 'nix uniformly into the overall invention composition. More importantly, unlike Ti-based alloys, the high density of the niobium, and to some degree, the Zr, improves the overall density of the composition. This reduces the tendency of the desirable, but heavier Mo, to settle or segregate during the melting process, thus producing a more uniform and predictable composition in the invention Nb-based alloy.

Thus the invention Nb-based alloy comprises Nb, Ti, Zr and Mo with about 29 to 70 weight percent Nb, about 10 to 46 weight percent Zr, and where Mo is between about 3 and 15 weight percent, and where the balance is titanium. The shaded area on the NbTiZr teranary phase diagram (FIG. 7d) shows the approximate range of these three constituents in the invention niobium alloy. However the presence of Mo, also included in the composition of the invention alloy, strongly stabilizes the beta phase and thus produces a relatively stable beta alloy at temperatures below 500° C. versus the alpha plus beta phase shown at 500° C. in the NbTiZr teranaly diagram. The exceptionally stable beta phase has been demonstrated on a Nb 35Ti 25Zr 5Mo composition, in which the beta transus was determined to be below 225° C. with only 5 percent Mo.

The preferred embodiment, is aNbTiZrMo alloy, with 35 weight percent Ti, 25 weight percent Zr, and 5 weight percent Mo. This preferred composition has mechanical properties summarized in Table 2.

TABLE 2

Mechanical properties of Nb35Ti25Zr5Mo alloy of the present invention

| Condition | Tensile Str. (ksi) | Yield Str (ksi) | Elong. (%) | Reduction In Area (%) | Elastic Modulus (msi) |
|---|---|---|---|---|---|
| Annealed | 135 | 125 | 16 | 49 | 13 |
| Strip, 50% c.w. | 161 | 151 | 6 | 49 | 11 |
| Strip, 56% | 172 | 165 | 8 | 46 | 11 |
| Wire, 63% | 174 | 170 | 7 | 61 | 9 |
| Wire, 90% c.w. | 214 | 157 | 6 | — | 5 |

The ability of the Ti, Zr, and Mo at this level allows the invention Nb alloy to be melted in a more uniform manner, and to attain a full beta structure with a unique combination of exceptionally high tensile strength and exceptionally low modulus in the cold-worked (c.w.) condition. No commercially available Ti alloys used for dental or other medical devices exhibit this unique combination of properties with the exception of TiNi shape memory alloys. However, the invention NbTiZrMo alloy specifically excludes the allergic effects of nickel and is not a shape memory alloy. Further, TiNi alloys in the low modulus condition (also about 5 msi) do not have the exceptional strength exhibited by the invention Nb-based alloy.

As shown in Table 2 above, the inventive alloy can be easily cold worked to increase strength and reduce the elastic modulus. The amount of zirconium added to the alloy is of an amount sufficient to produce a more sluggish transformation of beta during cooling, thus lowering the beta transus to improve toughness and phase uniformity, favorable for improved corrosion resistance. Zr also provides improved radiopacity, and allows the invention alloy to form a hard, abrasion-resistant conversion surface oxide or nitride through standard oxidation and nitriding methods known by those skilled in the art. The presence of a hard, inert, abrasion resistant ceramic surface layer in the invention alloy presents an important option for medical implants and devices in which it is desirable to have lower friction and wear, improved cutting ability, electrical insulation and improved corrosion resistance. This improved oxidation resistance of the invention alloy is a reflection of the ability of the zirconium to more readily oxidize and control the surface layer properties than Nb or Ti and thus, lower the potential for hydrogen to defuse into the alloy, if hydrogen is present during a conversion hardening process. Hydrogen can be detrimental to titanium alloys by the potential formation of hydrides formed during the conversion hardening process. Typical conversion hardening temperatures for the inventive alloy include a range from between about 300° C. to 700° C. for oxidation and from a range between about 700° C. to 1100° C. for nitridization. The time at temperature can be varied depending on the desired amount of oxide or nitride on the surface. Because the invention NbTiZrMo alloy forms a full beta structure at these temperatures, the conversion surface layer will be more uniform and functional.

As mentioned previously, the addition of molybdenum to a titanium alloy can reduce the elastic modulus of the alloy with a minimum in modulus at about 6 weight percent Mo. Mo can also improve corrosion resistance of an implant manufactured from the inventive alloy, particularly in reducing-type, low pH environments, such as those created by passive oxide film damage in crevices in modular implants. Zirconium can also improve corrosion resistance due to it's more reactive, stable passive surface oxide. This phenomenon is well described by Pourbaix. Although titanium and zirconium in a niobium alloy can be beneficial with respect to medical devices, the additional presence of molybdenum can be expected to provide even greater benefits in the invention alloy.

Metallurgically, as mentioned previously, zirconium can provide marginal strengthening of titanium alloys, and can stabilize the beta phase, via lowering the beta transus to produce a more sluggish transformation. Niobium is also a strong beta stabilizer, but molybdenum is even stronger. Formability of an alloy improves if the beta transus can be lowered to maintain a relatively stable beta phase at 500° C. and below. Further, molybdenum provides strengthening and corrosion resistance in the invention NbTiZrMo alloy.

Because of the advantages and limitations described above, the preferred invention titanium alloy composition includes niobium (about 29 to 70 weight percent) with about between 3 to 15 weight percent molybdenum and with between about 10 to 46 weight percent zirconium, and the balance titanium; but where neither the Zr or Ti exceed the amount of Nb in the alloy. Further, interstitial oxygen, nitrogen or carbon can be increased for additional interstitial strengthening of the invention alloy.

The invention alloy is usefull in the manufacturing of a variety of medical implants and devices. The manufacture of medical devices from the invention alloy includes orthodontic wire, brackets and other related orthodontic devices, endodontic files, and dental implant devices and components. The manufacture of medical devices also includes orthopaedic implants, including bone fracture plates, screws, compression hip plates and lag screws, intramedulary rods, staples, and various internal and external tissue fixation devices. Other orthopaedic implant devices include spinal plates, screws, and rods, ear implant (ENT) devices, and total joint and surface replacement devices. Examples of cardiovascular devices made from the invention alloy include vascular stents, vena cava filters, annuloplasty rings, vascular and other grafts, aneurysm clips and coils, heart valves, artificial hearts and ventricular assist devices, pacemakers and electrical signal canying leads, power containers, sensors, and percutaneous devices. Similarly the invention alloy is useful for neuro devices, bone graft substitute, various surgical instruments including cutting instruments, needles, guide and delivery wires and couplers, flexible catheters, guide wires, and surgical cables. To improve bio-compatibility of the medical implant or device made from the inventive alloy, at least a portion of the surface of the invention alloy can be conversion surface hardened and /or coated. Such coatings can include, but are not limited to, antibiotics, pro- or anti-thrombogenic agents, anti-inflammatory agents, morphogenic proteins, morphogenic peptides, growth factors, or stem cells.

Selected examples of implants which can be made using the invention NbTiZrMo alloy are described below. Certain aspects of the invention may be more readily understood with reference to the accompanying figures, all of which are not to scale but are for illustrative purposes only.

Figure 1A:
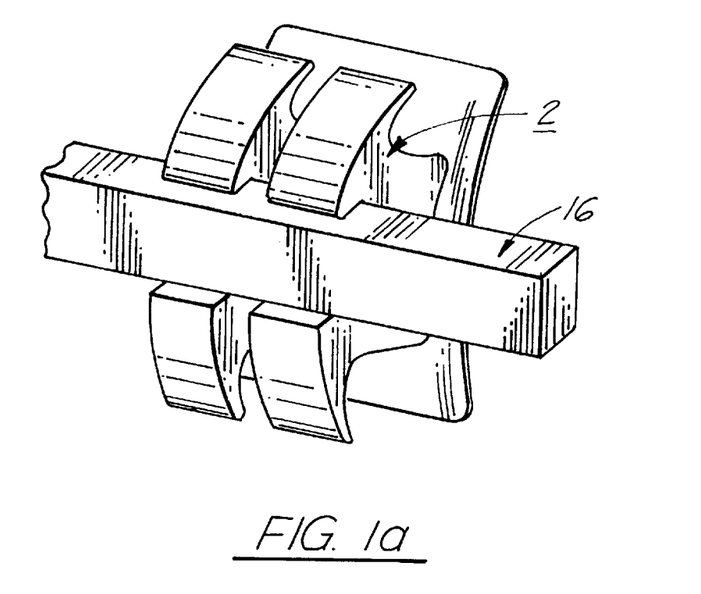
FIG. 1a is a perspective view of an orthodontic dental bracket engaged with the arch wire.
Figure 1B:
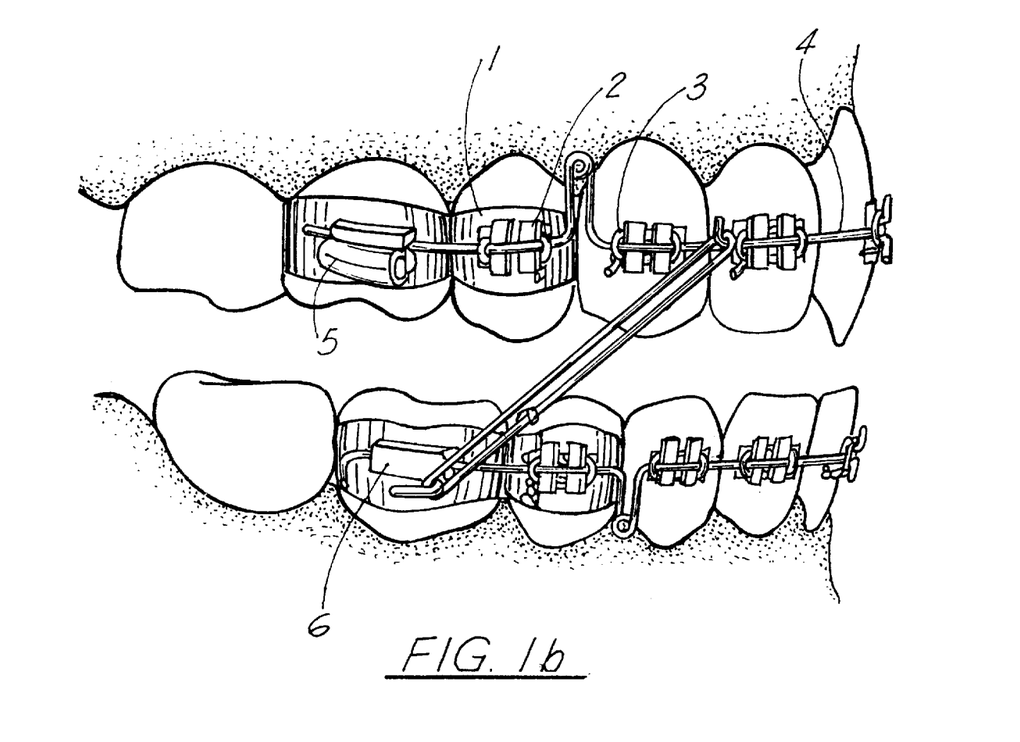
FIG. 1b is a schematic view of various orthodontic devices engaged on the teeth.
Figure 2:
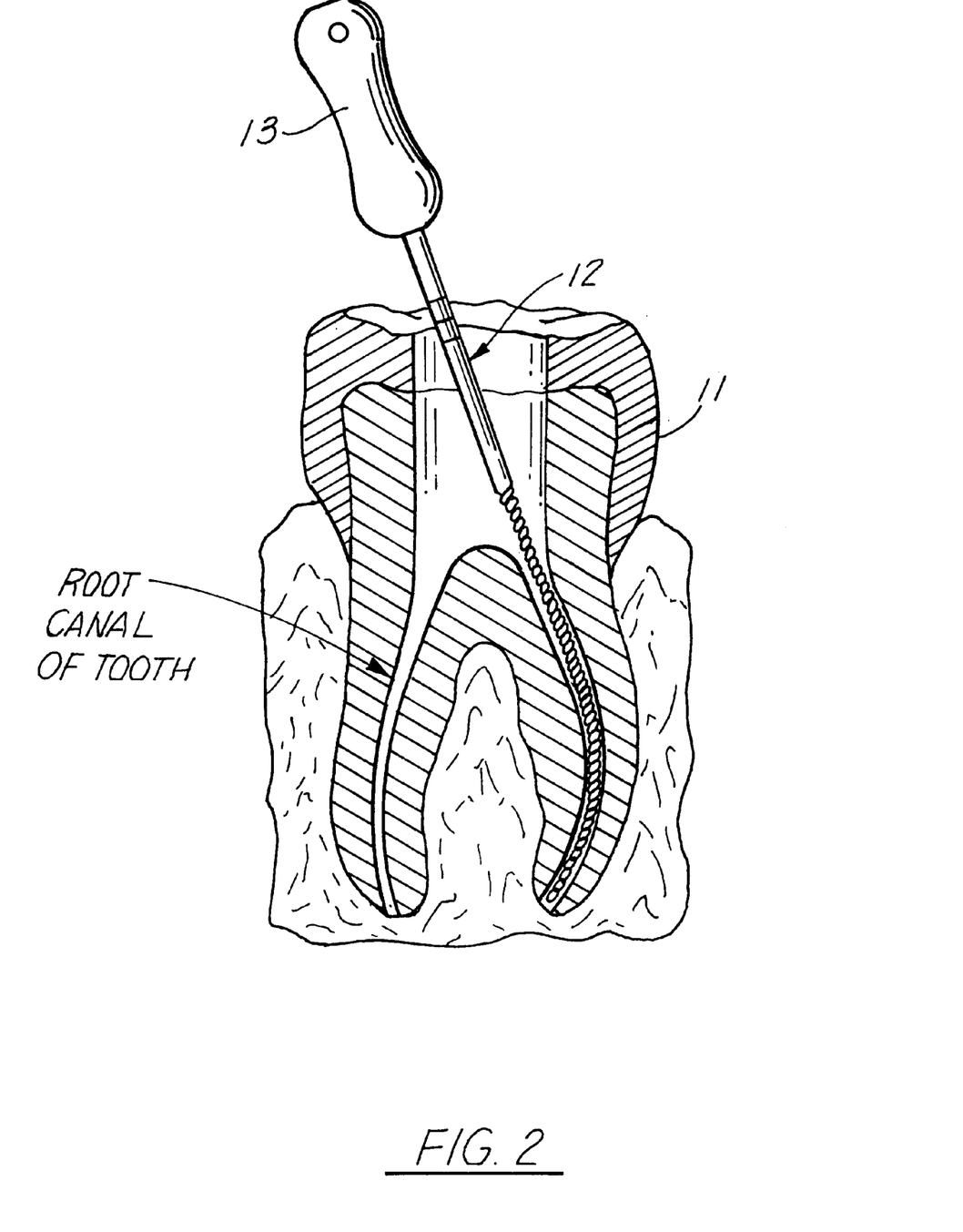
FIG. 2 is a cross-sectional schematic view of a typical endodontic dental file used for root canal procedures, engaged in the root of a tooth.

FIG. 1a shows an orthodontic archwire 16 engaged with a bracket 2 which in some cases can be attached to other orthodontic devices (FIG. 1b) including bands 1 tie wires 3, head-gears 5 and buccal tubes 6. The combination of high strength and flexibility of the invention alloy is well suited for the manufacture of arch wire which can exert a desirable gentle but continuous force for movement of teeth. FIG. 2 is an illustration showing an endodontic file 12 engaged in the canal of a root in a tooth 11. The combination of high-strength and low modulus of the invention alloy results in a lower device stress when engaged with the curved root geometry.

Figure 3A:
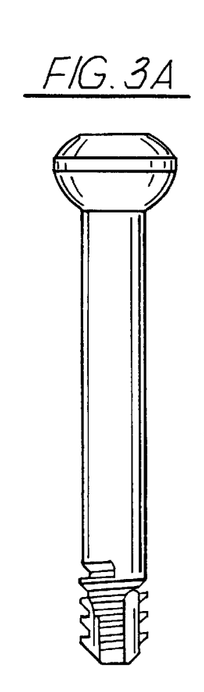
FIG. 3a is a plan side view of a typical screw for affixing a bone plate to bone for fracture repair.
Figure 3B:
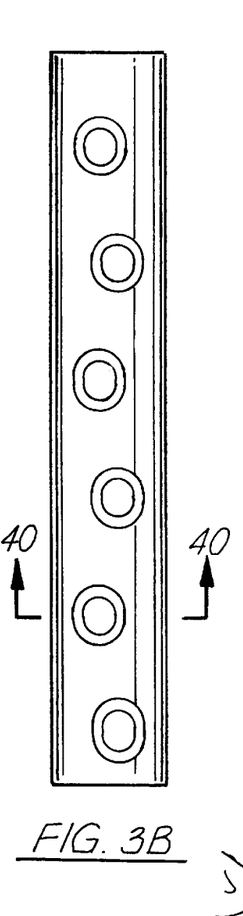
FIG. 3b is a plan top view of a typical bone plate.
Figure 3C:
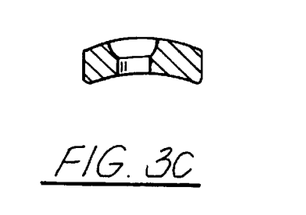
FIG. 3c is a cross-section of FIG. 3b taken along line 40.

FIG. 3a shows a typical bone screw manufactured from the invention alloy. FIG. 3b shows a typical plate affixed by the screws. FIG. 3c is a cross-sectional view of the bone plate shown in FIG. 3b taken along line 40. The higher strength and flexibility of the invention alloy will reduce stress shielding of the underlying bone.

Figure 4:
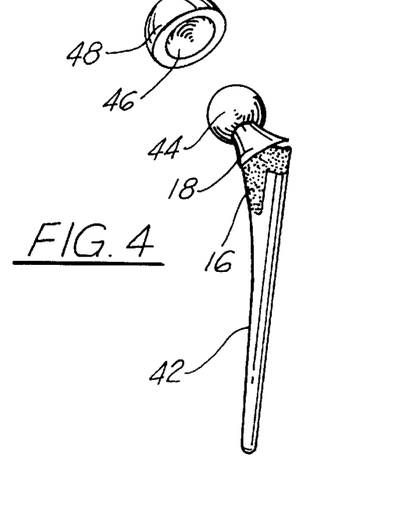
FIG. 4 is a perspective view of components of a typical hip joint prosthesis.

A typical hip joint assembly fabricated from this invention alloy is shown in FIG. 4. The hip joint stem 42 fits into the femur while the femoral head 44 of the prosthesis fits onto the stem neck and articulates against the inner polymer lining 46 of an acetabular cup 48 which in turn is affixed to the pelvis (not shown). A porous metal bead or wire mesh coating of the invention alloy 16 may be incorporated to allow stabilization of the implant by in-growth of surrounding tissue into the porous coating. Similarly, such a coating can also be applied to the acetabular component. The femoral head 44 may be an integral part of the hip joint stem 42 or may be a separate component from the invention alloy mounted upon a conical taper at the end of the neck 18 of the hip joint prosthesis. The conversion oxide option of the invention alloy can allow for a hard, hydrophillic ceramic surface of the bearing surface, which has been shown clinically to reduce friction and wear of the counter polymer bearing surface.

Figure 5:
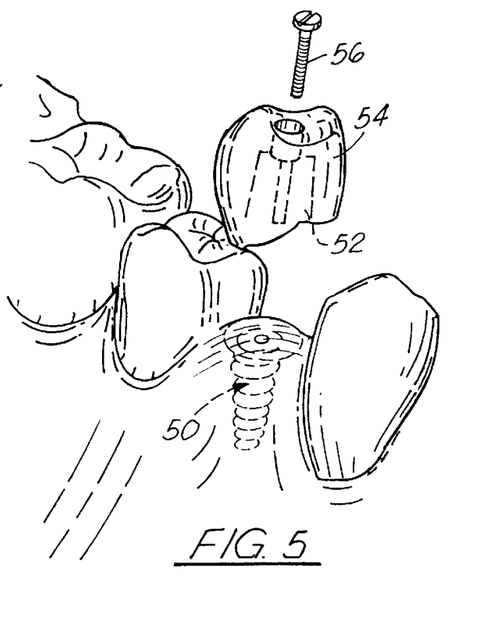
FIG. 5 is a schematic view in partial cross section of a gum with a dental implant fabricated from the NbTiZrMo alloy according to the present invention.

FIG. 5 shows a dental implant fixture 50 of the invention alloy implanted into a jaw bone. The fixture 50 is capped with an abutment 52 of the invention alloy for receiving a crown 54. In a typical implantation procedure, assuming that the original tooth has been removed, an incision is made into the gum above the implant site. The site is prepared by peeling back gum tissue and drilling into the jawbone. A fixture is then screwed or pressed into place in the jawbone and the site is covered for about 3 to 6 months to allow bone to grow around the implant and stabilize it in the jaw bone. After this period, the top of the fixture 50 is exposed and an abutment 52 as attached to the fixture. A crown 54, having a socket corresponding to the abutment, is then anchored to the abutment using an abutment screw 56, of the invention alloy to complete the method of implantation. The fixture 50 is prepared from the invention alloy. The abutment 52 and any screws 56 are also fabricated from the invention alloy. The crown 54 is fabricated to include an abutment made from the invention alloy that is suitably coated to provide the appearance of a natural tooth. The combination of high strength and flexibility of the invention alloy will improve load transfer and engagement with surrounding bone and improve resistance to fracture.

Figure 6:
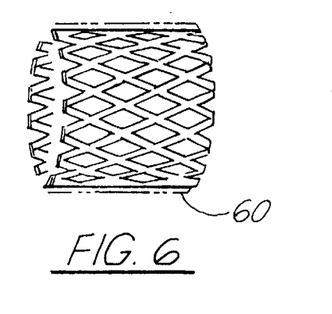
FIG. 6 is a perspective view of an expanded vascular stent for treating blocked blood vessels in the body.

FIG. 6 shows the use of the invention NbTiZrMo alloy for a vascular stent 60. Although the figure shows an expandable type stent 60, the invention alloy is also useful for self-expanding stents.

Figure 7A:
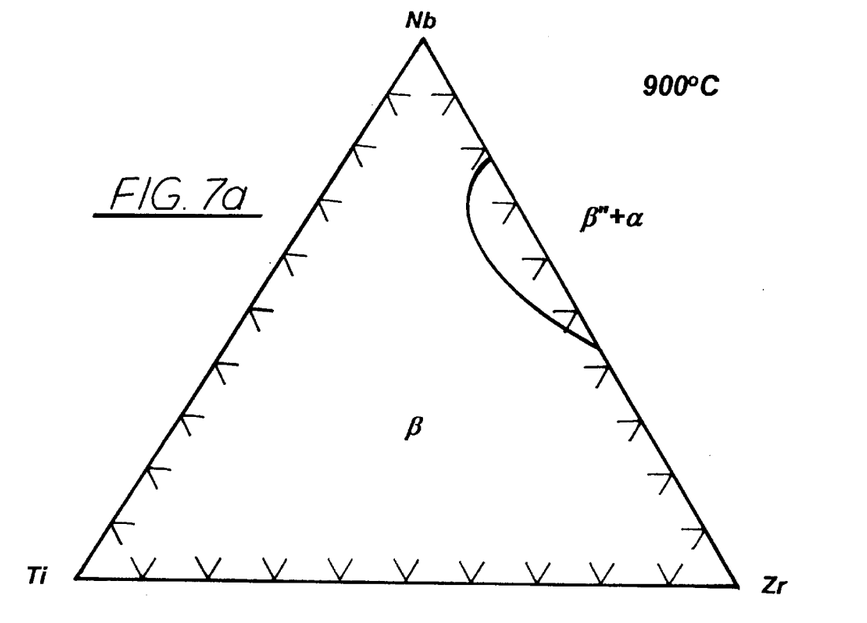
FIG. 7a is an isothermal cross-section of the NbTiZr ternary phase diagram at 900° C.
Figure 7B:
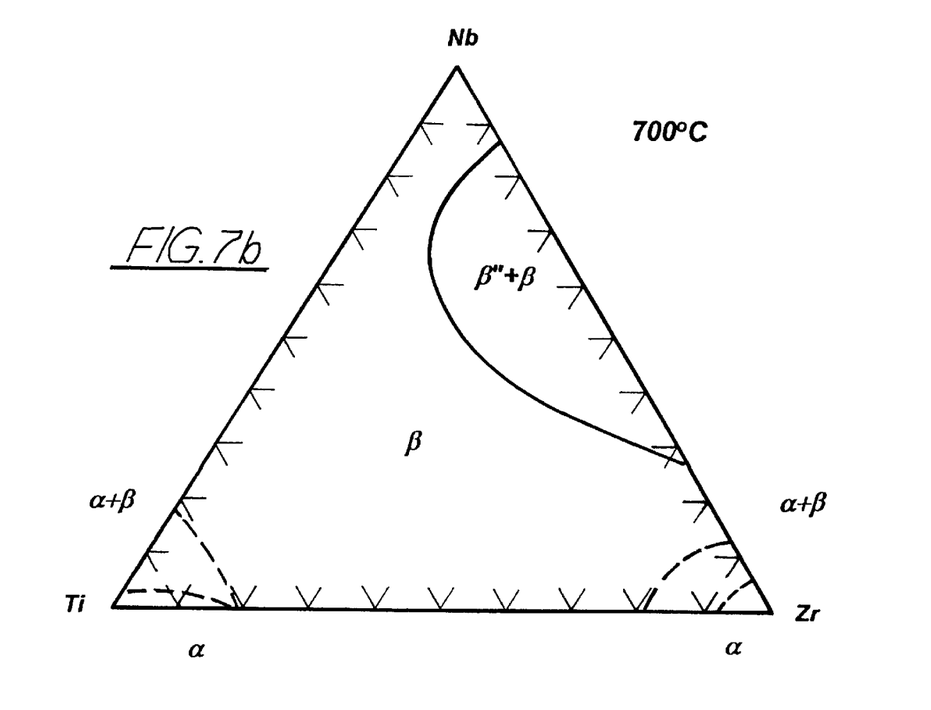
FIG. 7b is FIG. 7a at an isothermal cross-section of the NbTiZr ternary phase diagram at 700° C.
Figure 7C:
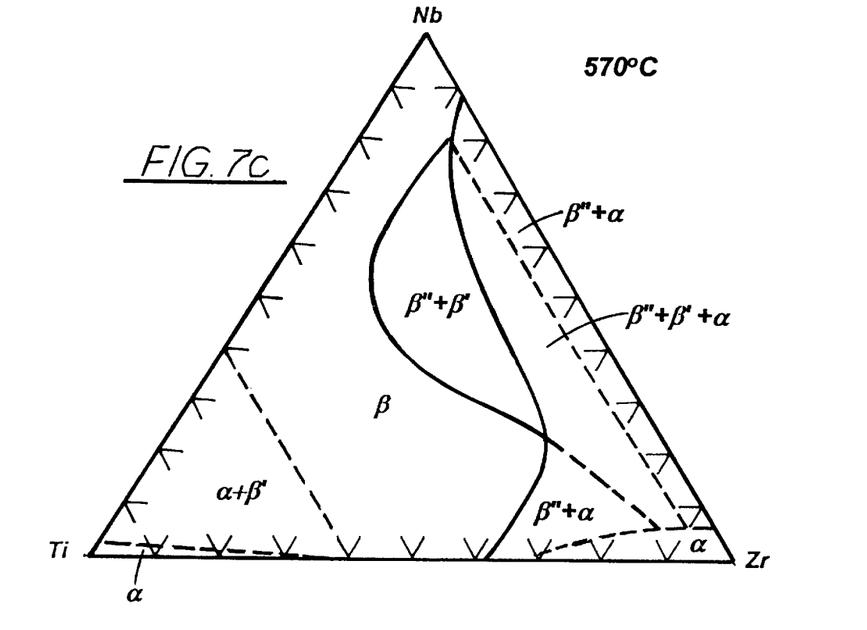
FIG. 7c is FIG. 7a at an isothermal cross-section of the NbTiZr ternary phase diagram at 570° C.
Figure 7D:
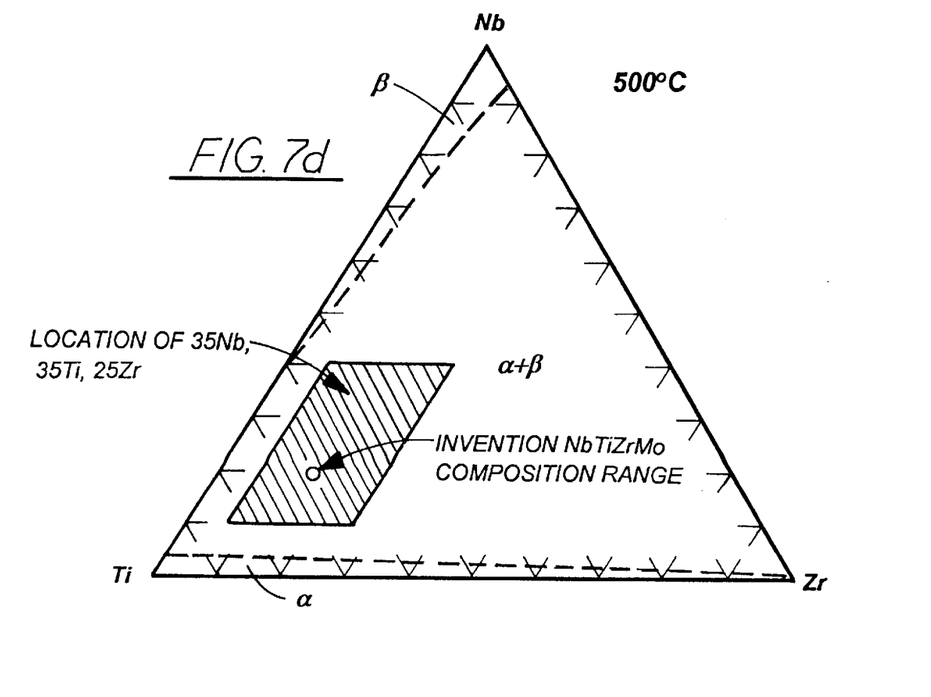
FIG. 7d is FIG. 7a at an isothermal cross-section of the NbTiZr ternary phase diagram at 500° C.

FIG. 7a shows an isothermal section of the NbTiZr ternary phase diagram at 900° C. At this temperance the invention alloy is a full beta structure even without Mo. FIG. 7b is an isothermal at 700° C. showing the necessity of Mo to stabilize beta, as for the case at 570° C. and 500° C. (FIGS. 7c and 7d).

The present invention is the use of specific combinations of Nb,Ti,Zr, and Mo to produce a niobium-based alloy for medical implants and devices. Biologically adverse elements such as Co, Cr, Ni, V, Be, and Al are specifically and intentionally excluded in the invention composition. To optimize melting and compositional uniformity, and to produce a tough corrosive-resistant, beta phase alloy which can be readily cold-worked to produce a desirable combination of high strength and low modulus; and to further, enable the alloy to be oxidized or nitrided to form a hard conversion oxide or nitride surface layer, the preferred compositional range of the NbTiZrMo alloy is as follows: Niobium between about 29 and 70 weight percent, zirconium between about 10 and 46 weight percent, molybdenum between about 3 and 15 weight percent, and the balance titanium. This invention composition relative to the Nb, Zr, and Ti is shown as a shaded region in FIG. 7d. Notice that the Nb—Zi—Ti ternary phase diagram isotherms shown in FIG. 7d is given in atomic percent, and not weight percent of each element. The presence of about 3 to 15 weight percent Mo in the invention alloy further stabilizes the preferred beta phase structure at lower temperatures. Molybdenum is a strong beta stabilizer in this alloy system. The preferred composition of the invention alloy is one with about 35 weight percent Nb, about 35 weight percent titanium, about 25 weight percent zirconium, and about 5 weight percent molybdenum. This composition is shown by the closed circle in FIG. 7d. Although FIG. 7d shows the preference of a alpha-plus-beta structure, it has been shown that the presence of only 5 weight percent Mo produces a full beta structure at this temperature and at room temperature as well based on the beta transus analysis described previously.

The subject invention discloses the benefits or use of a Nb-based NbTiZrMo alloy for any device application, whether medical or non-medical. Thus the invention NbTiZrMo alloy can also be used for various non-medical product applications requiring high-strength, flexible, and corrosion and wear resistant performance characteristics.

Although the present invention has been described with reference to its preferred embodiments, those skilled in the arts will recognize changes that may be made in form and structure which do not depart from the spirit of the invention already described in the specification and embodied in the claims which follow.

What is claimed is:

1. A medical implant or deve fabricated from a niobium (Nb)—titanium (Ti)—zirconium (Zr)—Molybdenum (Mo) alloy (NbTiZrMo alloy), said medical implant or device comprising:

components at least partially fabricated from a metal alloy consisting of:
(a) between about 29 and 70 weight percent Nb
(b) between about 10 and 46 weight percent Zr
(c) between about 3 and 15 weight percent Mo
(d) and a balance of titanium;
   wherein no other alloy exceeds the amount of Nb, and the alloy provides for a uniform beta structure which is uniform and corrosion resisting, and is capable of being readily processed to develop high-strength and low-modulus, with the ability for conversion oxidation or nitridization surface hardening of the medical implant or device.

2. A medical implant or device of claim 1, wherein the alloy further allows up to about 3 weight percent contaminants of at least one element selection from the group consisting of Si, P, Cu Fe, Ta, Hf, Sn, and Pd.

3. A medical implant device of claim 1, further comprising at least one intersticial strengthening element selected from the group consisting of oxygen, nitrogen, and carbon.

4. A medical implant or device of claim 1, wherein the alloy composition is niobium with about 35 weight percent titanium, about 25 weight percent zirconium, and about 5 weight percent molybdenum.

5. A medical implant or device of claim 1, wherein at least a portion of said implant or device has been surface hardened by a process selected from the group consisting of oxidation, nitriding and carbonitriding to form a hard, diffusion-bonded, conversion surface oxide, nitride or carbonitride.

6. A medical implant or device of claim 1, wherein at least a portion of said implant or device has been surface hardened by a process selected from the group consisting of oxygen diffusion hardening or nitrogen diffusion hardening, leaving a metallic-type appearance.

7. The medical implant or device of claim 1, wherein at least a portion of a surface of said implant or device is coated with a low-friction coating.

8. The medical implant or device of claim 1, wherein at least a portion of a surface of the implant or device is coated with an agent to improve hemo-compatibility; soft tissue attachment, or bone attachment, said agent selected from the group consisting of antibiotics, anti-thrombogenics, pro-thrombogenics, anti-inflammatories, morphogenic proteins, peptides, growth factors, stem celles, hyaluronan, and polyethylene glycol.

9. The medical implant or device of claim 1, wherein the medical implant or device is selected from a group consisting of an orthodontic, endodontic, dental implant, and other dental device.

10. The medical implant or device of claim 1, wherein the medical implant or device is an orthopaedic device selected from a group consisting of devices for joint replacement, tissue anchoring, bone substitute, trauma repair, spinal fixation and repair, maxillo-facial and cranial repair, or middle ear and drain tube devices.

11. The medical implant or device of claim 1, wherein the medical implant or device is a cardiovascular device selected from a group consisting of a vascular stent, heart valve, annuloplasty ring, heart pump or assist device, pacing or defibrilation lead wires, and flexible delivery or guide wires.

12. A medical implant or device of claim 1, wherein the implant or device is shaped as an orthodontic arch wire.

13. A medical implant or device of claim 1, wherein the implant or device is shaped as an orthodontic bracket for a attachment to a human tooth.

14. A medical implant or device of claim 1, when the implant or device is shaped as an endodontic file configured for root canal insertion.

15. A medical implant or device of claim 1, wherein the implant or device is shaped as a fixture for implantation into a jaw bone.

16. A medical implant or device of claim 1, wherein the implant or device comprises components at least partially fabricated from metal alloys falling within the shaded area of FIG. 7D.

17. A niobium (Nb)—titanium (Ti)—zirconium (Zr)—molybdenum (Mo) alloy (NbTiZrMo alloy), consisting of:
   (a) between about 29 and 70 weight pent Nb
   (b) between about 10 and 46 weight percent Zr
   (c) between about 3 and 15 weight percent Mo
   (d) up to about 3 wt. % of one or more contaminant elements each selected from the group consisting of Si P, Cu, F, Ta, Hf, Sn and Pd, up to about 1 wt % each; and
   (e) a balance of titanium;
wherein no other alloy constituent excoedis the amount of Nb.

* * * * *